(12) United States Patent
Stanhope et al.

(10) Patent No.: US 8,721,589 B1
(45) Date of Patent: May 13, 2014

(54) ENDOTRACHEAL TUBE CUFF INFLATION DEVICE AND METHODS

(75) Inventors: Rawley Stanhope, Dover, NJ (US); Brandon W. Close, Olathe, KS (US)

(73) Assignee: Spiritus Technologies, LLC, Lenexa, KS (US)

( * ) Notice: Subject to any disclaimer, the term of this patent is extended or adjusted under 35 U.S.C. 154(b) by 270 days.

(21) Appl. No.: 12/957,101

(22) Filed: Nov. 30, 2010

Related U.S. Application Data

(60) Provisional application No. 61/265,205, filed on Nov. 30, 2009, provisional application No. 61/418,266, filed on Nov. 30, 2010.

(51) Int. Cl.
*A61M 29/00* (2006.01)

(52) U.S. Cl.
USPC ................................. 604/96.01; 604/99.02

(58) Field of Classification Search
USPC .................... 604/181, 96.01, 99.02, 98.01
See application file for complete search history.

(56) References Cited

U.S. PATENT DOCUMENTS

| | | | |
|---|---|---|---|
| 4,064,879 A | 12/1977 | Leibinsohn | |
| 4,178,938 A | 12/1979 | Au | |
| 4,178,940 A | 12/1979 | Au | |
| 4,367,739 A | 1/1983 | LeVeen et al. | |
| 4,370,982 A | 2/1983 | Reilly | |
| 4,475,906 A | 10/1984 | Holzner | |
| 4,624,659 A | 11/1986 | Goldberg et al. | |
| 4,924,862 A * | 5/1990 | Levinson | 128/207.16 |
| 5,015,233 A | 5/1991 | McGough et al. | |
| 5,074,443 A | 12/1991 | Fujii et al. | |
| 5,163,904 A | 11/1992 | Lampropoulos et al. | |
| 5,270,685 A | 12/1993 | Hagen et al. | |
| 6,605,064 B2 | 8/2003 | Hatch | |
| 7,273,053 B2 * | 9/2007 | Zocca et al. | 128/207.14 |

FOREIGN PATENT DOCUMENTS

WO 98/25663 6/1998

OTHER PUBLICATIONS

Alexander H. Slocum, Jr., et al, Design of a Pressure Measuring Syringe, Proceedings of the 2010 Design of Medical Devices Conference, Apr. 13-15, 2010, Cambridge, MA.
Papiya Sengupta et al, Endotracheal Tube Cuff Pressure in Three Hospitals, and The Volume Required to Produce an Appropriate Cuff Pressure, BMC Anesthesiology, Nov. 29, 2004, United States.
M.O. Abdelatti et al, A Cuff Inflator for Tracheal Tubes, Anaesthesia 1997, pp. 765-769, Department of Anaesthesia, Edgware General Hospital, Edgware, Middlesex UK.

* cited by examiner

*Primary Examiner* — Kevin C Sirmons
*Assistant Examiner* — Deanna K Hall
(74) *Attorney, Agent, or Firm* — Kutak Rock LLP; Bryan P. Stanley

(57) ABSTRACT

The present general inventive concept relates to a syringe that, when connected to an endotracheal tube (ETT) cuff, automatically inflates the ETT cuff to a safe pressure in a single, full stroke of the syringe, and methods related thereto. The syringe includes a plunger, body, high pressure valve and low pressure valve. The syringe inflates an ETT cuff to a pressure high enough to seal the ETT cuff in a patient's trachea, but not high enough to cause damage. Then the pressure is reduced to a desired optimal pressure by releasing pressure through the low pressure valve.

20 Claims, 4 Drawing Sheets

ENDOTRACHEAL TUBE CUFF INFLATION DEVICE AND METHODS

CROSS REFERENCES

This application claims the benefit of, and priority based upon, U.S. Provisional Patent Application Ser. No. 61/265,205, entitled "SYRINGE," filed Nov. 30, 2009, the entire disclosure of which is herein incorporated by reference.

This application claims the benefit of, and priority based upon, U.S. Provisional Patent Application Ser. No. 61/418,266, entitled "ENDOTRACHEAL TUBE CUFF INFLATION DEVICE AND METHODS," filed Nov. 30, 2010, the entire disclosure of which is herein incorporated by reference.

FIELD

The present invention relates to a endotracheal tube cuff inflation device. More specifically, the present invention is concerned with a syringe that, when connected to an endotracheal tube (ETT) cuff, automatically inflates the ETT cuff to a safe pressure in a single, full stroke of the syringe.

BACKGROUND

Healthcare professionals in General Anesthesia, Intensive Care and Emergency Medicine use over 60 million ETTs a year to manage patient airways. The vast majority of ETTs utilize an inflatable cuff that forms a pneumatic seal with the patient's trachea to prevent air leakage and aspiration during patient ventilation after the ETT has been placed in the patient's trachea through intubation. Multiple studies suggest that maintaining cuff pressure at 20-30 cm H2O is critical for patient safety; pressures below 20 cm H2O have been shown to increase the risk of Ventilator Associated Pneumonia (VAP) and pressures above 30 cm H2O are associated with a higher risk of stenosis, ischemia and rupture of the trachea. Despite the severity and high costs of these complications, unsafe cuff pressures have been observed in over half of intubated patients at numerous hospitals and EMT units.

There are two conventional techniques to inflate an ETT cuff: (1) subjective feedback based on the pressure of the external palpation balloon and (2) inflating a set volume of air based on the selected cuff size. These methods have been shown to be inaccurate even in the hands of experienced professionals. Studies comparing hospitals with high and low rates of unsafe cuff pressures have found that hospitals using pressure meters to check cuff pressure upon inflation outperformed hospitals relying on conventional techniques utilizing no peripheral instrumentation.

Some hospitals use a Cufflator or similar blood pressure meter to measure and monitor cuff pressure. The Cufflator is an analog pressure gauge attached to a compressible rubber handle that, when squeezed, acts as a bellow and inflates the cuff. The Cufflator is bulky, expensive, and has been shown to be inaccurate by as much as 4 cm H2O. Consequently, many hospitals prefer to use blood pressure meters in conjunction with a T-valve and a syringe. Although less expensive and more accurate than the Cufflator, connecting these three devices together to inflate the cuff introduces more procedural time. Set-up time aside, both the Cufflator and blood pressure meter require training; (1) users must know the proper pressure to leave the cuff and (2) users must know to inflate the cuff to an excessively high pressure before lowering it to the final pressure. The latter requirement is an accepted practice of experienced Respiratory Therapists to establish a creaseless seal between the cuff and the trachea.

U.S. Pat. Nos. 4,367,739, 4,370,982, 5,074,443, 5,270,685, 5,163,904, 4,064,879, 4,624,659, 4,475,906, 6,605,064, 4,178,938 4,178,940, and 5,015,233, the entire disclosures of which are incorporated herein by reference, illustrate several prior art syringes and other apparatuses that have been used for inflating ETT cuffs and which suffer from the disadvantages discussed above. Therefore, it would be beneficial to provide an accurate, reliable, and/or cost efficient means to automatically establish a safe ETT cuff pressure.

There is a long-felt, unmet need for an improved apparatus and related methods for inflating an ETT cuff to a safe pressure. The present general inventive concept provides an accurate, reliable, and/or cost efficient means to automatically establish a safe ETT cuff pressure with a single full stroke of the syringe.

SUMMARY

According to one aspect, an endotracheal tube cuff inflation device is provided. The device includes a syringe body and a syringe plunger slidably positioned within the syringe body for creating a fluid (air) pressure within said body. It further includes a high pressure valve for releasing an excess volume of fluid (air) from the body once the fluid pressure within the body reaches a predetermined high pressure limit and to temporarily maintain it. It further includes a low pressure valve for releasing fluid (air) pressure from the body, after the high pressure limit has been maintained, to reduce the fluid (air) pressure within the body from the predetermined high pressure limit to a predetermined low pressure limit. In some embodiments, the high pressure and low pressure valves are embedded within the body. In other embodiments, the high pressure valve is embedded within the plunger. It will be appreciated that in alternative embodiments, the low pressure valve may be embedded within the plunger (either alone, or in combination with the high pressure valve).

According to a second aspect, an endotracheal tube cuff inflation device is provided. The device includes a syringe plunger sized and shaped to slide along the inside of a syringe body. The plunger includes an end sized and shaped to engage with the inside of the body such that a fluid (air) seal is formed between the end of the plunger and the inside of the body, and a volume of fluid is expelled from the body through an orifice in one end of the body as the plunger is inserted further into the body and a volume of fluid is taken in to the body as the plunger is drawn out of the body. The device further includes a high pressure valve sized, shaped, and configured to release an excess volume of fluid from the body after the fluid pressure within the body reaches a predetermined high fluid pressure. The predetermined high fluid pressure is sufficient to inflate an endotracheal tube cuff to a point where a pneumatic seal is formed between the endotracheal tube cuff and a patient's trachea to prevent air leakage and aspiration during patient ventilation. The device further includes a low pressure valve sized, shaped, and configured to release an excess volume of fluid from the body to reduce the fluid pressure within the body from the predetermined high fluid pressure to a predetermined low fluid pressure. The predetermined low fluid pressure is high enough to minimize increased risk of Ventilator Associated Pneumonia and low enough to minimize increased risk of stenosis, ischemia and rupture of the trachea. The low pressure valve is sealed, initially, until after the fluid pressure within the body reaches the predetermined high fluid pressure. After the predetermined high fluid pressure is reached, the seal on the low pressure valve is broken such that the fluid pressure within the body is reduced from the predetermined high fluid pressure to the predetermined low fluid pressure.

A single full stroke of the plunger in the body begins at an initial point where the plunger has been drawn out from the body to the fullest extent possible without breaking the fluid seal that is formed between the end of the plunger and the inside of the body. In some embodiments, a stop is included within the body to prevent removal of the plunger from the inside of the body and ensure the fluid seal that is formed between the end of the plunger and the inside of the body is not broken. The single full stroke ends at a concluding point where the plunger has been inserted within the body to the fullest extent possible without breaking the fluid seal that is formed between the end of the plunger and the inside of the body.

In some embodiments, the low pressure valve is sized, shaped, and configured to release any fluid pressure buildup in the body (over the course of a single full stroke) generally in excess of about 20 cm H2O to 30 cm H2O. In some embodiments, the high fluid pressure is in the range of generally 60 to 90 cm H2O. In some embodiments, the body includes a fluid volume capacity generally greater than the fluid volume capacity of an endotracheal tube cuff. In some embodiments, the low pressure valve is sealed by a membrane. In some embodiments, the membrane is punctured by the plunger, exposing the low pressure valve and reducing the fluid pressure within the body from the predetermined high fluid pressure to the predetermined low fluid pressure. In some embodiments, fluid flow through the orifice is sealed off after the fluid pressure within the body reaches the predetermined low fluid pressure. In some embodiments, fluid flow through the orifice is sealed off after a period of time (e.g., 3 seconds) after the single full stroke has concluded.

According to a third aspect, a method of using an endotracheal tube cuff inflation device is provided. The method of use includes drawing out the syringe plunger from the syringe body, connecting the orifice to an endotracheal tube cuff, and inserting the syringe plunger into the syringe body in a single full stroke to create a fluid pressure within said body. The inserting step includes the steps of: releasing an excess volume of fluid from said body once said fluid pressure within said body reaches a predetermined high pressure limit and to temporarily maintain said predetermined high pressure limit within said body; and releasing fluid pressure from said body after said high pressure limit has been maintained to reduce said fluid pressure within said body from said predetermined high pressure limit to a predetermined low pressure limit. In some embodiments, the method further includes sealing off the endotracheal tube cuff inflation device after the fluid pressure within the syringe body is reduced from the predetermined high fluid pressure to the predetermined low fluid pressure.

One embodiment of the instant invention comprises a disposable syringe that, over the course of a single, full stroke of the syringe plunger, will increase cuff pressure, from a generally deflated pressure (approximately 0 cm H2O, or some other suitable pressure below 25 cm H2O) to over 60 cm H2O (or another suitable predetermined high pressure limit, including but not limited to other limits discussed in other embodiments herein) and then decrease the pressure to a final pressure of 25 cm H2O (or another suitable predetermined low pressure limit, including but not limited to other limits discussed in other embodiments herein). The initial pressure overshoot of 60 cm H2O is achieved with a high pressure relief valve, optionally located at the tip end of the syringe, which releases air when the syringe chamber pressure reaches (or exceeds) 60 cm H2O. The syringe chamber volume is larger than the volume of the ETT cuff the syringe is being used to inflate such that the 60 cm H2O pressure relief valve will be activated before the syringe plunger is fully contracted. In some embodiments, at the end of the syringe plunger stroke, and preferably after the ETT cuff has been inflated to 60 cm H2O in the manner described above, the plunger punctures a membrane, thereby exposing a second pressure relief valve that releases air until the pressure drops to 25 cm H2O.

In another embodiment of the general inventive concept, the syringe used to inject fluid (air) into an Endotracheal Tube cuff (ETTc) to the proper pressure of 25 cm H2O (or other predetermined limit) is comprised of a plunger that slides up and down a chamber in a reciprocating piston arrangement to force air out of the chamber through a male luer nozzle that connects to a standard female luer of the ETTc portal. The syringe has two unique sub-systems that work together to set the cuff pressure to 25 cm H2O, namely the "Low Valve Activation" and "Reseal" sub-systems.

In the Low Valve Activation sub-system, the syringe uses a unique arrangement of passive fluid pressure valves to reach the proper pressure of 25 cm H20 by (stage 1) exceeding the final pressure during the plunger stroke and (stage 2) dropping to the final pressure with a passive valve that is activated at the end of the syringe stroke, allowing air to flow out of system.

In the Low Valve Activation, Stage 1, during the stroke of the syringe, air is injected into the ETTc until the cuff is fully inflated. The volume of the syringe chamber is larger than the volume of the cuff to ensure the cuff will be fully inflated to pressures exceeding final pressure (preferably 60-90 cm H2O, or other desired predetermined limit) before the plunger travels the distance of a single, complete stroke. To avoid unsafe over-pressurization of the ETTc, air is allowed to escape out of a high pressure passive valve, in this embodiment calibrated to open at pressures around 90 cm H2O (or other predetermined high pressure limit). In one preferred embodiment, the high pressure valve is seated in the plunger. Alternative embodiments have the high pressure valve seated within the syringe chamber. Regardless of where the high pressure valve is physically located, it is arranged such that fluid pressure within the syringe chamber (cavity formed between the body and the plunger) that exceeds the high pressure valve limit is released.

In the Low Valve Activation, Stage 2, at the end of the plunger stroke, the plunger activates a low pressure valve that was previously sealed off from the airflow through the system. Once activated, air escapes out of the over-pressurized ETT cuff through the low pressure valve. In this embodiment, the Low Valve is calibrated such that fluid pressure immediately decreases until it reaches 25 cm H2O. Consequently, in a preferred embodiment, during Stage 2, the pressure of the system follows an exponential curve that falls sharply the instant the Low Valve is activated. In a preferred embodiment, after a predetermined period of time (e.g. approximately 3 seconds in one embodiment) after the Low Valve is activated, system pressure levels out around 25 cm H2O. In this preferred embodiment, the Low Valve is isolated from the system by a spring-loaded piston member (referred to as the Low Valve Actuator hereon) that seals off the volume around the low valve with an o-ring. When the plunger nears the end of its stroke, it pushes down the Low Valve Actuator, the O-ring seal is broken and air can flow through the Low Valve out of the syringe chamber.

In the reseal, since the airflow out of the Low Valve will continue (through eventual bleeding of the valve) until the system pressure drops to near zero, the syringe includes a method of shutting off the airflow when the pressure has fallen to 25 cm H2O. Since the pressure drops to 25 cm H2O approximately 3 seconds after the Low Valve is activated, the Reseal mechanism has an approximate 3 second delay before the system completely reseals. In the preferred embodiment, the Reseal mechanism is comprised of a spring-loaded piston (separate from the Low Valve Actuator and referred to as the Flow Actuator hereon) with an O-ring that shuts off flow through the male luer nozzle. The Flow Actuator slides inside the Plunger. As the Plunger is pushed down during the syringe stroke, friction from the Plunger pushes the Flow Actuator down against the spring thereby breaking the o-ring seal and allowing air to flow out the nozzle. At the end of a syringe stroke, the spring pushes the Flow Actuator back up to until the Flow Actuator O-ring is in its sealed position. The spring is calibrated so that the returning force placed upon the Flow Actuator is slightly greater that the friction of the Plunger on the Flow Actuator. Consequently, the Flow Actuator slowly travels upward toward the reseal position (3 second total travel time). I will be appreciated that alternative delay periods may be utilized without departing from the spirit and scope of the instant invention.

In some preferred embodiments, in which the syringe of the present general inventive concept is intended to be used with, and is used with, a standard ETT cuff used on adults, the syringe volume prior to breaking the seal of the second (low) pressure relief valve (i.e. by breaking a membrane covering the seal, activating a piston to open the seal or otherwise exposing the low pressure valve) is approximately 13 ml. This volume is designed to be larger than the volume of the standard ETT cuff, and allows the syringe of this embodiment to work with a large variety of ETT cuffs, including ETT cuffs that are used in the animal life sciences. There is a linear relationship between measured cuff pressure (cm H2O) and the volume of air in the cuff (ml), defined as: Pressure=7.5*Volume+2.7. Based upon this equation, the minimum syringe volume necessary to inflate the standard ETT cuff to 60 cm H2O is approximately 7.64 ml. Thus, the syringe volume of approximately 13 ml of the preferred embodiment discussed herein helps to ensure proper inflation of a standard ETT cuff to 60 cm H2O, by taking into account outliers from the study discussed in Appendix B and producing a volume of air that is significantly greater than the volume typically necessary to inflate the ETT cuff to 60 cm H2O, and thereby utilizing the 60 cm H2O pressure release valve to prevent the cuff pressure from exceeding 60 cm H2O.

The embodiments of the present general inventive concept discussed above provide healthcare professionals with means to automatically establish a safe ETT cuff pressure with a single stroke of a syringe. The present general inventive concept automatically establishes a safe pressure, thereby eliminating risk and procedural time associated with conventional methods of ETT cuff inflation. In addition, the device of the embodiment discussed herein is disposable and lightweight, both of which are qualities valued in hospital setting. The automatic syringe of the embodiment discussed herein may eliminate, or help to reduce, hospitals' durable medical equipment costs, procedural time and procedural risk. Hospitals continue to cut costs by incorporating disposable devices into patient care; disposables may be billed to the patient, reduce inventory costs and do not require periodic calibration (as do ETT cuff pressure measurement devices such as the Cufflator). Meanwhile, hospitals are faced with the constant challenge of reducing risk to the patient, which often requires increased durable medical equipment spending and procedure duration. Nevertheless, the instant invention provides a novel device that has the advantage of reducing both patient risk and hospital cost. Some embodiments of the general inventive concept are intended to be single use only and afterward disposed of. Other embodiments of the general inventive concept are intended to be disposable after a patient no longer needs it, but may be used and re-used repeatedly on a single patient (for example, the syringe may be re-used if the proper seal was not achieved on the first try or if the ETT Cuff needs to be re-inflated).

The foregoing and other objects are intended to be illustrative of the general inventive concept and are not meant in a limiting sense. Many possible embodiments of the invention may be made and will be readily evident upon a study of this specification and accompanying drawings comprising a part thereof. Various features and subcombinations of general inventive concept may be employed without reference to other features and sub combinations. Other objects and advantages of the general inventive concept will become apparent from the following description taken in connection with the accompanying drawings, wherein is set forth by way of illustration and example, an embodiment of this invention.

BRIEF DESCRIPTION OF THE DRAWINGS

These and/or other aspects and utilities of the present general inventive concept will become apparent and more readily appreciated from the following description of the embodiments, taken in conjunction with the accompanying drawings. For the purpose of illustration, forms of the present general inventive concept which are presently preferred are shown in the drawings; it being understood, however, that the general inventive concept is not limited to the precise arrangements and instrumentalities shown. In the drawings.

DETAILED DESCRIPTION

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Preferred embodiments of the instant invention are discussed herein in the context of a syringe 10. The syringe includes a plunger 20 and a body 30 (or tube or barrel) in which the plunger tightly fits. The syringe is a simple piston pump. The plunger is pulled and pushed along inside the body, allowing the syringe to take in and expel a fluid through an orifice 31 at the open end of the tube and/or through other orifice(s) into the tube. In some embodiments, fluid is allowed to expel out of the syringe through orifice 31, but is prevented from being taken in to the syringe body through orifice 31. In such embodiments, other orifice(s) are provided to allow air to be taken into the syringe body. In the preferred method described herein the fluid is air. In some embodiments, the open end of the syringe is fitted with a tubing to help direct the flow of air into (and in some embodiments, out of) the barrel and into an ETT cuff that is inflated by the syringe. In other embodiments, the open end of the syringe is a nozzle or male luer sized and shaped to engage with a standard female luer of an ETT cuff. The syringe body is sized such that the fluid volume of the body is greater than the fluid volume of the ETT cuff.

Figure 1:
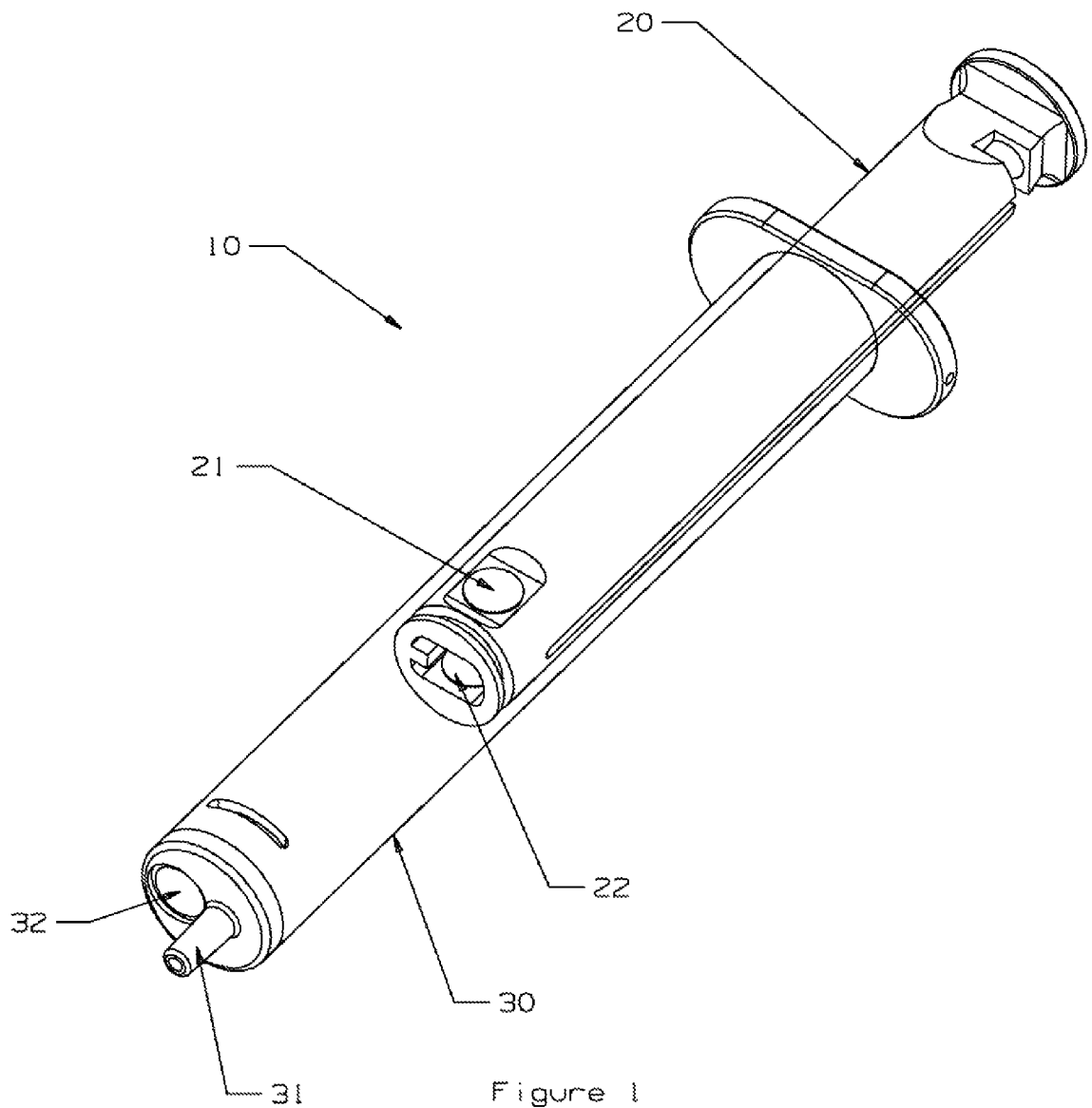
FIG. 1 is a perspective view of a syringe of a preferred embodiment of the general inventive concept with the body of the syringe shown as being transparent.

Referring to the accompanying Drawings, FIGS. 1-9 represent a first embodiment of the general inventive concept. FIG. 1 is a perspective view of a syringe of a preferred embodiment of the general inventive concept with the body of the syringe shown as being transparent. FIG. 1 shows a syringe body and a syringe plunger slidably positioned within the syringe body for creating a fluid (air) pressure within said body. The embodiment shown in FIG. 1 further includes a high pressure valve 21 for releasing an excess volume of fluid (air) from the body once the fluid pressure within the body reaches a predetermined high pressure limit and to temporarily maintain it. It further includes a low pressure valve 32 for releasing fluid (air) pressure from the body, after the high pressure limit has been maintained, to reduce the fluid (air) pressure within the body from the predetermined high pressure limit to a predetermined low pressure limit. It further includes a one-way valve 22 for allowing fluid (air) to be drawn into the body when the plunger is pulled upward from the body. In FIG. 1, the high pressure valve 21 and one-way valve 22 are both embedded within the plunger, and low pressure valve 32 is embedded within the body. Nevertheless, it will be appreciated that the location of any or all valves may within either the plunger or the body without departing from the spirit and scope of the instant invention.

Figures 2, 3, 4:
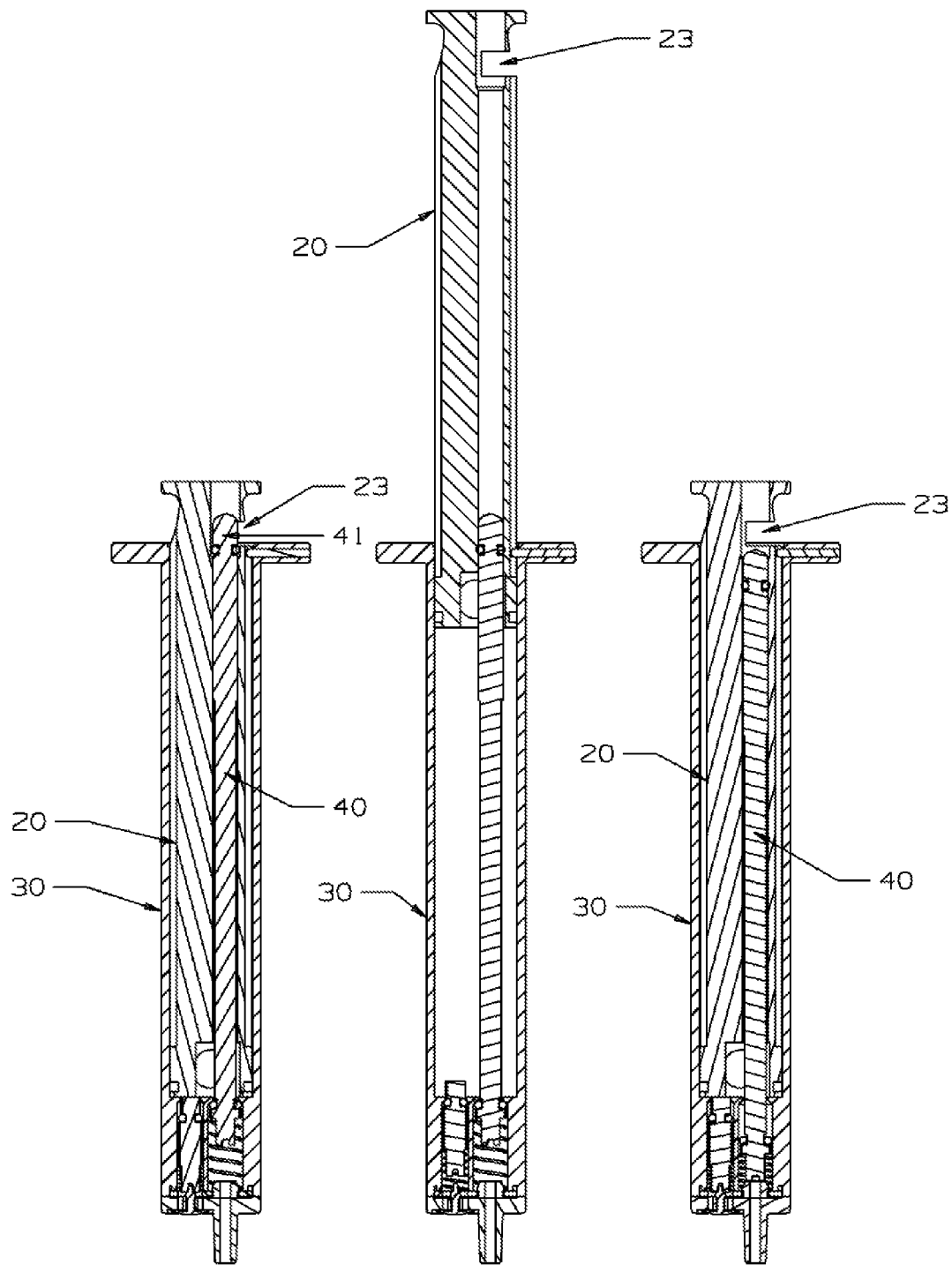
FIG. 2 is a lengthwise cross-sectional view of the syringe of FIG. 1 with the plunger in a fully inserted position.
FIG. 3 is a lengthwise cross-sectional view of the syringe of FIG. 1 with the plunger in a fully withdrawn position.
FIG. 4 is a lengthwise cross-sectional view of the syringe of FIG. 1 with the plunger in a fully inserted position, but before the luer is sealed off.

FIGS. 2-4 show lengthwise cross-sectional views of the syringe of FIG. 1 with the plunger in various positions while in use. In FIG. 2, the plunger is shown fully inserted within the syringe body. The plunger includes a generally hollow cavity in which a spring-loaded piston Flow Actuator 40 is positioned and allowed to slide up and down within the plunger cavity. The spring-loaded piston Flow Actuator 40 maintains frictional engagement with one or more walls (or other members) of the plunger, so that downward movement of the plunger 20 will also push Actuator 40 downward. The spring-loaded piston Flow Actuator 40 is shown in a position where the male luer nozzle is sealed off (i.e. piston up). This allows the ETT cuff to achieve and maintain a final operating fluid pressure of the desired level without any further pressure bleed at the syringe valves. In FIG. 3, the plunger is shown fully extracted and the single full stroke of the plunger is about to begin. In FIG. 4, the single, full stroke of the plunger has been completed but the male luer nozzle is not yet sealed off as shown by the down position of the spring-loaded piston Flow Actuator. After a period of time, preferably about three seconds, the spring loaded piston Flow Actuator shown in FIG. 4 will return to the position shown in FIG. 2, thus sealing off the male luer nozzle. As is shown in FIG. 2, the plunger includes a view window 23 (notch or cutout) that allows a user to see within the plunger cavity and see the top 23 of the spring-loaded piston Flow Actuator 40 when it is in its upward, sealed-off position to confirm that the re-seal has been completed.

Figure 5:
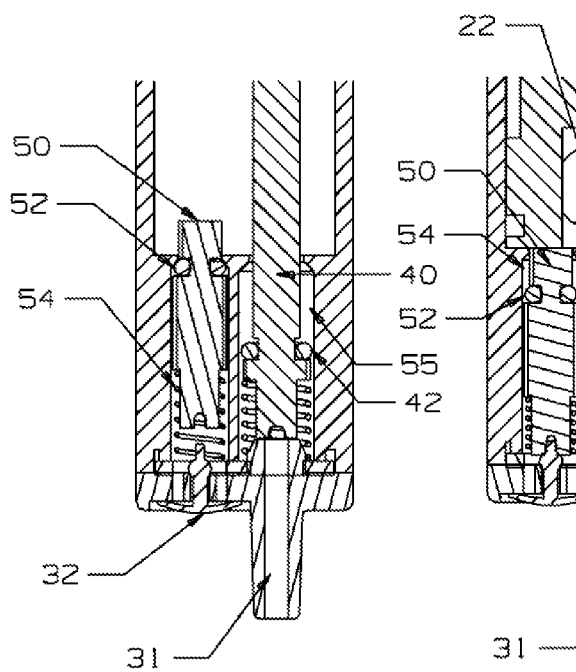
FIG. 5 is an enlarged lengthwise partial cross-sectional view of the tip of the syringe of FIG. 1 with the plunger withdrawn.
Figure 6:
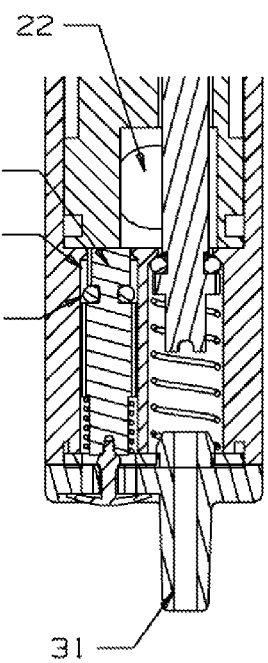
FIG. 6 is an enlarged lengthwise partial cross-sectional view of the tip of the syringe of FIG. 1 with the plunger fully inserted and engaging with the low pressure valve.
Figure 7:
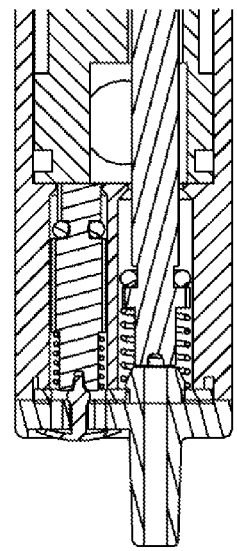
FIG. 7 is an enlarged lengthwise partial cross-sectional view of the tip of the syringe of FIG. 1 with the plunger fully inserted and fluid pressure of the luer sealed off.

FIGS. 5-7 show enlarged lengthwise cross-sectional views of the tip of the syringe of FIG. 1 with the plunger in various positions. The low pressure valve (and spring-loaded low valve actuator) are shown on the left in FIGS. 5-7 and the spring-loaded piston Flow Actuator is shown on the right in FIGS. 5-7.

In FIG. 5, the plunger is extracted, at least partially, from the body of the syringe. The low pressure valve has not been activated and is sealed off from the rest of the syringe chamber in FIG. 5 by the spring-loaded low valve actuator 50. The spring-loaded low valve actuator 50 includes o-ring 52 that forms a seal between the interior cavity of the body 30 of the syringe and cavity 54 in which the low pressure valve 32 and the spring of the spring-loaded low valve actuator 50 are located. As the plunger 20 is pushed down into body 30, a lip located toward the lower end of the plunger engages the top of actuator 50 and pushes actuator 50 downward, causing the o-ring to move downward from its sealed position and exposing cavity 54 and low pressure valve 32 to the fluid pressure that has been created within the syringe body 30.

Also in FIG. 5, the spring-loaded piston Flow Actuator 40 is shown in its down/open position (resulting from the downward motion of the plunger and the frictional engagement between the plunger 20 and the Flow Actuator 40). As is shown in FIG. 5, the Flow Actuator 40 includes an o-ring 42 that forms a seal between the interior cavity of the body 30 of the syringe 10 and cavity 55 in which the opening to orifice/luer 31 is located to allow air to be expelled from the syringe of the instant invention. The spring of Flow Actuator 40 is also located within cavity 55.

In FIG. 6, the plunger is fully inserted within the syringe body. The plunger engages with the spring-loaded low valve actuator to break the seal to the low pressure valve. The system releases fluid pressure until it reaches the desired low pressure point, preferably about 25 cm H2O.

In FIG. 7, after a period of time, the spring-loaded piston Flow Actuator slides back along through a channel within the plunger (against the friction force created between the plunger and the piston) and the fluid flow through the male luer nozzle of the syringe is sealed off by o-ring 42 which engages the top of cavity 55. Any fluid pressure bleed via either the high valve or the low valve is sealed off from the ETT cuff (and the tip of the syringe), and fluid (air) is prevented from being drawn into the syringe body through luer 31. This is because cavity 55 is sealed off from the inner cavity of body 30 in which plunger 20 is located. Thus, air is drawn into body 30 through one-way valve 22.

Figure 8:
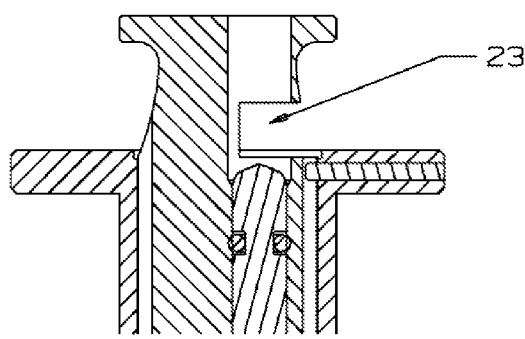
FIG. 8 is an enlarged lengthwise partial cross-sectional view of the end of the syringe of FIG. 1 with the plunger fully inserted, but before the luer is sealed off.
Figure 9:
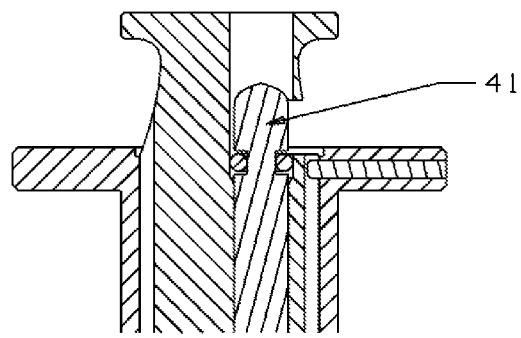
FIG. 9 is an enlarged lengthwise partial cross-sectional view of the end of the syringe of FIG. 1 with the plunger fully inserted, after the luer is sealed off.

FIGS. 8-9 show enlarged lengthwise cross-sectional views of the end of the syringe of FIG. 1 with the plunger fully inserted. FIG. 8 shows the spring-loaded Flow Actuator in its unsealed position. FIG. 9 shows the spring-loaded Flow Actuator after a period of time, after the syringe fluid flow outlet is sealed off. FIGS. 8-9 show a "window" 23 in the plunger so that a user can easily identify whether the fluid flow through the syringe tip has been sealed off (FIG. 9) because the top 41 of Flow Actuator 40 is visible in the window and thus the ETT cuff has reached desired operating pressure. The user can also easily and quickly identify if the fluid flow through the syringe tip has not yet been sealed off (FIG. 8), indicating that the ETT cuff may still need to release some pressure to achieve desired operating pressure.

In some embodiments, the syringe body is generally circular in cross section; however, it will be appreciated that the shape of the syringe may vary without departing from the spirit and scope of the instant invention. The circular shape allows for easy assembly of the plunger and the body. In some embodiments, the plunger includes a framework that is generally "t" shaped in cross-section, and which includes a circular disk at the top end for pulling and pushing of the plunger by an operator. The bottom end of the plunger includes a generally circular disc or plug to create a pneumatic seal with the syringe body. The "t" shaped framework provides rigidity to the plunger.

Figure 10:
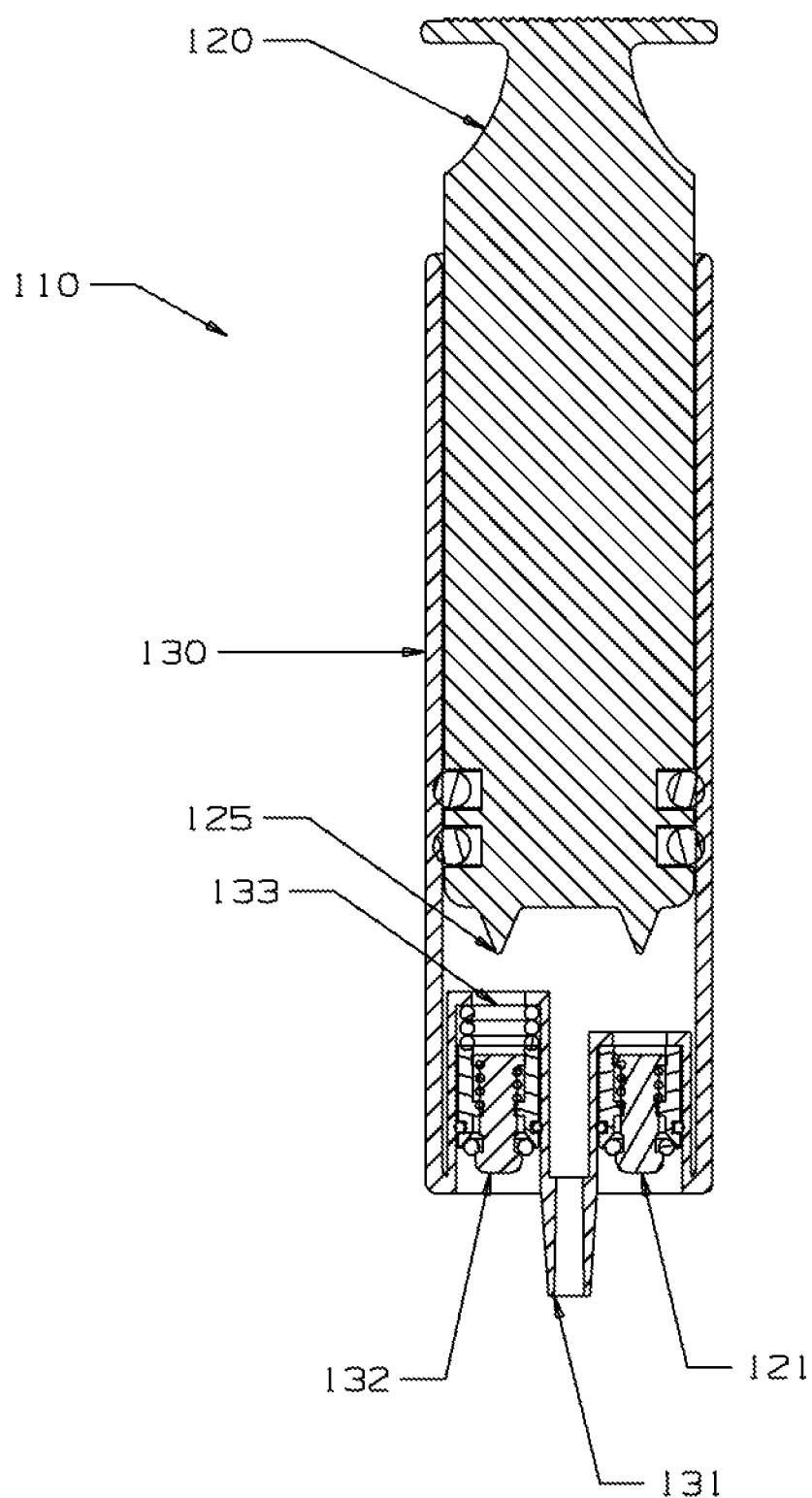
FIG. 10 is a lengthwise cross-sectional view of a syringe of another embodiment of the general inventive concept with the body of the syringe shown as being transparent.

Referring to FIG. 10, another embodiment of a syringe 110 the instant invention is shown which includes body 130, plunger 120 and leur 131 for expelling air from body 130. In FIG. 10 three of the four sides of the "t" shaped framework (left, right, and front sides as shown in FIG. 10, with the front side being perpendicular to or protruding from the left and right sides) are visible at the top of the plunger 120 outside of the body 130. In addition to providing rigidity, the left and right sides include structure that properly aligns the plunger within the body and which meters the travel of the plunger within the body. The alignment portion of the "t" shaped framework is not shown on in FIG. 10, but the portion metering travel of the plunger is shown in FIG. 10. The alignment portion comprises a vertical channel that is formed in the end of the portion of the framework. A pin (dowel) that extends horizontally toward the interior of the body at the top lip of the body extends into the channel to prevent rotation of the plunger within the body. The portion metering travel comprises a flexible rib including serrated or ramped teeth. A pin extending from the opposing side of the body as the alignment pin extends to contact the surface of the rib. During manufacture or assembly of the syringe, the travel metering pin is positioned in contact with the serrated teeth surface of the rib, and the plunger is positioned within the body in a partially contracted position as shown in FIG. 10. The pin engages a ledge formed above the top serrated tooth on the plunger to prevent the plunger from contracting all the way into the body. As the plunger is pulled up out of the body, the pin slides along the serrated teeth, and the ledge of each subsequent serrated tooth prevents the plunger from being pushed back downward into the body, until the pin passes over the bottom tooth. At the bottom of the last serrated tooth, a ramp angles toward the opposing surface of the rib, such that the pin transitions to the opposing surface of the rib. The opposing surface of the rib is generally smooth. Thus, the plunger can be pushed downward and the pin will slide along the surface. Also, in a preferred embodiment, the rib has some flexibility to allow the rib to flex around the pin. As the plunger is pushed downward, there are no further obstacles to prevent the plunger from being fully contracted into the body.

As shown in FIG. 10, at the bottom of the syringe body are a pair of pressure relief values (high pressure 121 and low pressure 132 or 25 cm H2O and 60 cm H2O, as is discussed above in connection with preferred embodiments), located in cylindrical chambers or bores within the bottom of the body (extending from the interior of the body to the exterior of the body). The 60 cm H2O valve is always open (active), to limit the pressure generated by the syringe to 60 cm H2O. The 25 cm H2O valve, however, is closed off (inactive) by a sealing membrane 133 that is positioned over the interior opening of the bore in which the valve is located. The bottom of the plunger includes a needle 125 that aligns with the bore to puncture the membrane. In a preferred embodiment the membrane is a generally brittle material, such as a plastic or aluminum foil, that will break without significant stretching of the material. This prevents the material from blocking the valve once it is broken. Also, in another preferred embodiment, the valve is located within the bore such that the top of the valve is further away from the interior opening of the bore than the length of the needle. This helps to ensure that the membrane will not be pushed into the valve, and also prevents the needle from damaging the valve. Once the membrane is broken, the pressure within the syringe is lowered to 25 cm H2O, and thus, the pressure within the cuff to which the syringe is connected is also lowered.

As is shown in FIG. 10, the plunger includes two needles at the bottom of the plunger, on opposing sides of the bottom plug. This allows the plunger to be installed within the body and aligned within the pins in either direction, thus eliminating the possibility that the plunger will be installed such that the needle will not align with the 25 cm H2O valve. Also, as is shown in FIG. 10, the bore for the low pressure valve is taller than the bore for the high pressure valve, to ensure the needle penetrates the membrane over the bore. Nevertheless, it will be appreciated that the bores may be equal in height without departing from the spirit and scope of the instant invention. As is shown in FIG. 10, a pair of o-ring gaskets surround the plug at the bottom of the plunger to help create the tight seal with the body and to allow the pump to function properly.

In a preferred embodiment, the body and plunger of the syringe are both a cast urethane material. In one such embodiment, the pins are a metal material that is inserted into bores within the body, or which are cast in place within the body. In a preferred method of manufacturing the instant invention, the mold is made of a urethane material and include metal inlays to form all the cavities in the chamber.

Thus, while the present invention has been shown in the drawings and fully described above with particularity and detail in connection with what is presently deemed to be the most practical and preferred embodiment(s) of the general inventive concept, it will be apparent to those of ordinary skill in the art that many modifications thereof may be made without departing from the principles and concepts set forth herein, including, but not limited to, variations in size, materials, shape, form, function and manner of operation, assembly and use.

It is also to be understood that the following claims are intended to cover all of the generic and specific features of the general inventive concept herein described, and all statements of the scope of the invention which, as a matter of language, might be said to fall therebetween. Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. An endotracheal tube cuff inflation device comprising:
a syringe body;
a syringe plunger slidably positioned within said syringe body for creating a fluid pressure within said body;
a high pressure valve positioned on said body or on said plunger for releasing an excess volume of fluid from said body once said fluid pressure within said body reaches a predetermined high pressure limit and to temporarily maintain said predetermined high pressure limit within said body; and
a low pressure valve positioned on said body or on said plunger for releasing fluid pressure from said body after said high pressure limit has been maintained to reduce said fluid pressure within said body from said predetermined high pressure limit to a predetermined low pressure limit.

2. The endotracheal tube cuff inflation device of claim 1, wherein said high pressure valve is embedded in said plunger.

3. An endotracheal tube cuff inflation device comprising:
a syringe plunger sized and shaped to slide along the inside of a syringe body, said plunger having an end sized and shaped to engage with the inside of said body such that a fluid seal is formed between said end of said plunger and the inside of said body, and a volume of fluid is expelled from said body through an orifice in one end of said body as said plunger is inserted further into said body and a volume of fluid is taken in to said body as said plunger is drawn out of said body; and
a high pressure valve positioned on said body or on said plunger, said high pressure valve being sized, shaped, and configured to release an excess volume of fluid from said body after the fluid pressure within said body reaches a predetermined high fluid pressure, said predetermined high fluid pressure being sufficient to inflate an endotracheal tube cuff to a point where a pneumatic seal is formed between the endotracheal tube cuff and a patient's trachea to prevent air leakage and aspiration during patient ventilation; and
a low pressure valve positioned on said body or on said plunger, said low pressure valve being sized, shaped, and configured to release an excess volume of fluid from said body to reduce the fluid pressure within said body from said predetermined high fluid pressure to a predetermined low fluid pressure, said predetermined low fluid pressure being high enough to minimize increased risk of Ventilator Associated Pneumonia and low enough to minimize increased risk of stenosis, ischemia and rupture of the trachea;
said low pressure valve being sealed, initially, until after the fluid pressure within said body reaches said predetermined high fluid pressure, and after said predetermined high fluid pressure is reached, said seal on said low pressure valve is broken such that the fluid pressure within said body is reduced from said predetermined high fluid pressure to said predetermined low fluid pressure; and
a single full stroke of said plunger in said body begins at an initial point where said plunger has been drawn out from said body to the fullest extent possible without breaking said fluid seal that is formed between said end of said plunger and the inside of said body and said single full stroke ends at a concluding point where said plunger has been inserted within said body to the fullest extent possible without breaking said fluid seal that is formed between said end of said plunger and the inside of said body.

4. The endotracheal tube cuff inflation device of claim 3, wherein over the course of a single full stroke, said low pressure valve is sized, shaped, and configured to release any fluid pressure buildup in said body generally in excess of a particular pressure, said particular pressure in the range of generally 20 cm H2O to 30 cm H2O.

5. The endotracheal tube cuff inflation device of claim 3, wherein over the course of a single full stroke, said low pressure valve is sized, shaped, and configured to release any fluid pressure buildup in said body generally in excess of 20 cm H2O.

6. The endotracheal tube cuff inflation device of claim 3, wherein said predetermined high fluid pressure is in the range of generally 60 to 90 cm H2O.

7. The endotracheal tube cuff inflation device of claim 3, wherein said predetermined low fluid pressure is in the range of generally 20 to 30 cm H2O.

8. The endotracheal tube cuff inflation device of claim 3, wherein said body includes a fluid volume capacity generally greater than the fluid volume capacity of an endotracheal tube cuff.

9. The endotracheal tube cuff inflation device of claim 3, wherein said low pressure valve is sealed by a membrane.

10. The endotracheal tube cuff inflation device of claim 9, wherein over the course of a single full stroke, after the fluid pressure within said body reaches said predetermined high fluid pressure, said membrane is punctured by said plunger, exposing said low pressure valve and reducing the fluid pressure within said body from said predetermined high fluid pressure to said predetermined low fluid pressure.

11. The endotracheal tube cuff inflation device of claim 3, wherein said high pressure valve is positioned on said plunger.

12. The endotracheal tube cuff inflation device of claim 3, wherein said high pressure valve is positioned within said body.

13. The endotracheal tube cuff inflation device of claim 3, wherein said low pressure valve seal is broken before and near said concluding point of said single full stroke.

14. The endotracheal tube cuff inflation device of claim 3, wherein over the course of a single full stroke, fluid flow through said orifice is sealed off after the fluid pressure within said body reaches said predetermined low fluid pressure.

15. The endotracheal tube cuff inflation device of claim 3, wherein fluid flow through said orifice is sealed off after a period of time after said single full stroke has concluded.

16. The endotracheal tube cuff inflation device of claim 15, wherein fluid flow through said orifice is sealed off after said period of time by a spring loaded piston within said body.

17. A method of using the endotracheal tube cuff inflation device of claim 3, said method comprising:
drawing out said syringe plunger from said syringe body;
connecting said orifice to an endotracheal tube cuff; and
inserting said syringe plunger into said syringe body in a single full stroke.

18. The method of claim 17, further comprising:
sealing off the endotracheal tube cuff inflation device after the fluid pressure within said syringe body is reduced from said predetermined high fluid pressure to said predetermined low fluid pressure.

19. The method of claim 17, further comprising:
sealing off the endotracheal tube cuff inflation device after a period of time after said single full stroke has concluded.

20. The method of claim 19, wherein said period of time after said single full stroke has concluded is about three (3) seconds.

\* \* \* \* \*